United States Patent
Ohno et al.

(10) Patent No.: US 9,206,099 B2
(45) Date of Patent: Dec. 8, 2015

(54) METHOD FOR PRODUCING HYDROGENATED BIPHENOL

(71) Applicant: DAICEL CORPORATION, Osaka-shi, Osaka (JP)

(72) Inventors: Mitsuru Ohno, Himeji (JP); Tomohiro Hashizume, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 14/391,334

(22) PCT Filed: Mar. 28, 2013

(86) PCT No.: PCT/JP2013/059239
§ 371 (c)(1),
(2) Date: Oct. 8, 2014

(87) PCT Pub. No.: WO2013/153957
PCT Pub. Date: Oct. 17, 2013

(65) Prior Publication Data
US 2015/0099901 A1    Apr. 9, 2015

(30) Foreign Application Priority Data

Apr. 9, 2012  (JP) ................................ 2012-088136

(51) Int. Cl.
| | |
|---|---|
| C07C 29/20 | (2006.01) |
| C07C 29/60 | (2006.01) |
| C07C 29/78 | (2006.01) |
| C07C 1/24 | (2006.01) |

(52) U.S. Cl.
CPC . *C07C 29/20* (2013.01); *C07C 1/24* (2013.01); *C07C 29/60* (2013.01); *C07C 29/78* (2013.01); *C07C 2101/14* (2013.01); *C07C 2101/16* (2013.01); *C07C 2527/055* (2013.01)

(58) Field of Classification Search
None
See application file for complete search history.

(56) References Cited

U.S. PATENT DOCUMENTS 8,115,043 B2 *   2/2012   Takai et al. ................... 585/639

FOREIGN PATENT DOCUMENTS

| DE | 602837 | 9/1934 |
|---|---|---|
| EP | 2 014 634 A1 | 1/2009 |
| JP | 1-156935 A | 6/1989 |
| JP | 3-275637 A | 12/1991 |
| JP | 4-279537 A | 10/1992 |
| JP | 2005-97274 A | 4/2005 |

OTHER PUBLICATIONS

International Search Report issued in PCT/JP2013/059239, mailed on May 28, 2013.
Wilds et al., "Steroid Analogs Lacking Ring C. III. Synthesis of 4-(trans-4'-Hydroxycyclohexyl)-cyclohexanone", Journal of the American Chemical Society, 1954, vol. 76, No. 7, pp. 1733-1736.

* cited by examiner

*Primary Examiner* — Brian J Davis
(74) *Attorney, Agent, or Firm* — Birch, Stewart, Kolasch & Birch, LLP

(57) ABSTRACT

Provided is a method for efficiently producing high-purity hydrogenated biphenol based on a simple method that can be industrially utilized using easily-available biphenol as a starting material. The method for producing hydrogenated biphenol according to the present invention is a method for producing hydrogenated biphenol by hydrogenating biphenol represented by the following formula (1):

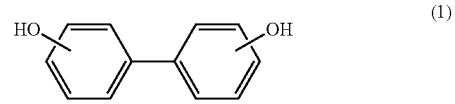

to obtain hydrogenated biphenol represented by the following formula (2):

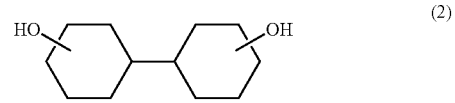

the method including: a reaction step of hydrogenating the biphenol represented by formula (1); and a purification step of washing or crystallizing a reaction product obtained from the reaction step using an aromatic hydrocarbon.

12 Claims, No Drawings

METHOD FOR PRODUCING HYDROGENATED BIPHENOL

TECHNICAL FIELD

The present invention relates to a method for producing high-purity hydrogenated biphenol that is useful as a fine chemical intermediate for pharmaceuticals, agricultural chemicals, electronic materials, and the like. The present application claims priority on the basis of Japanese Patent Application No. 2012-088136 filed in Japan on Apr. 9, 2012, the contents of which are incorporated herein by reference.

BACKGROUND ART

Conventionally, several methods have been known as methods for producing hydrogenated biphenol. In PTL 1, a portion of 4,4'-bicyclohexanol, which is the target hydrogenated bisphenol, is obtained using isopropanol as a solvent by hydrogenating bisphenol in the presence of 5% by weight of a Pd—C catalyst, filtering the reaction mixture, and removing the isopropanol from the filtrate by distillation under reduced pressure. At the same time, 4,4'-bicyclohexanol is also obtained by dissolving the crystals obtained during filtering in 500 mL of tetrahydrofuran when heating, then filtering and removing the tetrahydrofuran from the filtrate by distillation under reduced pressure. Further, the crystals from both of these processes are combined, suspended in n-hexane during heating, left to stand for 1 hour at 5 to 6° C., and the precipitated crystals are collected and dried under reduced pressure to obtain 4,4'-bicyclohexanol in a yield of 87%. Although the yield is sufficient, this method suffers from the drawback of complex operation.

On the other hand, PTLs 2 and 3 disclose a method in which, using one or two or more of glycol monoalkyl ethers having seven or less carbon atoms as a solvent, bisphenol is hydrogenated in the presence of a hydrogenation catalyst, the hydrogenation catalyst is then removed by filtering, and the solvent is removed from the filtrate by distillation under ordinary pressure or reduced pressure to produce hydrogenated biphenol. However, in this method, since a glycol monoalkyl ether having seven or less carbon atoms, which is a high-boiling point compound, is used as the solvent, the reaction system has to be put under reduced pressure and high temperature for the distillation, and thus as an industrial production method there is a problem of increased costs due to the large amount of energy required and the need to prepare high-performance equipment.

CITATION LIST

Patent Literature

PTL 1: Japanese Patent Laid-Open No. 01-156935
PTL 2: Japanese Patent Laid-Open No. 03-275637
PTL 3: Japanese Patent Laid-Open No. 04-279537

SUMMARY OF INVENTION

Technical Problem

Accordingly, it is an object of the present invention to provide a method for efficiently producing high-purity hydrogenated biphenol based on a simple method that can be industrially utilized using easily-available biphenol as a starting material.

It is another object of the present invention to provide a method for producing bicyclohexene, wherein hydrogenated biphenol is produced by the above-described method, and the obtained hydrogenated biphenol is dehydrated to obtain a corresponding bicyclohexene.

Solution to Problem

As a result of diligent research into solving the above problems, the present inventors discovered that by washing or crystallizing hydrogenated biphenol obtained by hydrogenating biphenol using an aromatic hydrocarbon as a poor solvent, the contained impurities can be easily removed, thereby enabling very high-purity hydrogenated biphenol to be obtained in a high yield. Based on this finding, the present inventors continued their research to complete the present invention.

Namely, the present invention provides a method for producing hydrogenated biphenol by hydrogenating biphenol represented by the following formula (1):

[Formula 1]

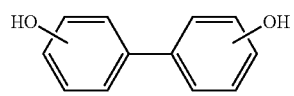
(1)

to obtain hydrogenated biphenol represented by the following formula (2):

[Formula 2]

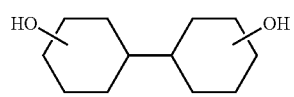
(2)

the method comprising: a reaction step of hydrogenating the biphenol represented by formula (1); and a purification step of washing or crystallizing a reaction product obtained from the reaction step using an aromatic hydrocarbon.

As the above-described biphenol, 4,4'-biphenol is preferred, and as the above-described hydrogenated biphenol, 4,4'-bicyclohexanol is preferred.

As the above-described aromatic hydrocarbon, toluene or 1,3,4-trimethylbenzene is preferred.

Further, the present invention provides a method for producing bicyclohexene, wherein hydrogenated biphenol is produced by the above-described method, and the obtained hydrogenated biphenol is dehydrated to obtain a corresponding bicyclohexene.

Advantageous Effects of Invention

According to the method for producing hydrogenated biphenol according to the present invention, hydrogenated biphenol having a very high purity can be efficiently produced by a simple operation. Consequently, the method for producing hydrogenated biphenol according to the present invention can be preferably used when producing high-purity hydrogenated biphenol on an industrial scale.

DESCRIPTION OF EMBODIMENTS

Method for Producing Hydrogenated Biphenol

The method for producing hydrogenated biphenol according to the present invention is a method for producing hydrogenated biphenol by hydrogenating biphenol represented by the following formula (1):

[Formula 3]

(1)

to obtain hydrogenated biphenol represented by the following formula (2):

[Formula 4]

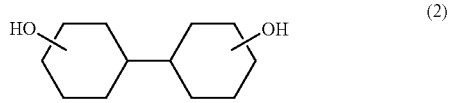
(2)

the method comprising: a reaction step of hydrogenating the biphenol represented by formula (1); and a purification step of washing or crystallizing a reaction product obtained from the reaction step using an aromatic hydrocarbon.

Examples of the biphenol represented by formula (1) used in the reaction include 2,2'-biphenol, 3,3'-biphenol, 4,4'-biphenol, 2,3'-biphenol, 2,4'-biphenol, 2,5'-biphenol, 3,4'-biphenol, and 3,5'-biphenol.

Examples of the hydrogenated biphenol represented by formula (2) may include a hydrogenated biphenol corresponding to the above-described biphenol represented by formula (1). For example, if 4,4'-biphenol is used as the biphenol represented by formula (1), the obtained hydrogenated biphenol represented by formula (2) is 4,4'-bicyclohexanol.

[Reaction Step]

The reaction step in the present invention is a step of hydrogenating the above-described biphenol represented by formula (1).

It is preferred to carry out the above-described hydrogenation reaction in the presence of a solvent. The solvent may be solvents capable of dissolving the biphenol represented by formula (1) that serves as a starting material, and examples include carboxylic acids such as acetic acid and propionic acid, and aliphatic alcohols such as methyl alcohol, ethyl alcohol, n-propyl alcohol, 2-propanol (isopropyl alcohol), n-butyl alcohol, s-butyl alcohol, t-butyl alcohol, n-amyl alcohol, isoamyl alcohol, n-hexyl alcohol, n-heptyl alcohol, and n-octyl alcohol. Among these, from the perspectives of excellent solubility of the substrate and being able to maintain catalytic activity, it is especially preferred to use a lower saturated aliphatic carboxylic acid such as acetic acid, or a primary saturated aliphatic alcohol such as methyl alcohol, ethyl alcohol, and 2-propanol. These solvents can be used singly or in combinations of two or more.

The amount of solvent to be used can be appropriately adjusted to, for example, based on 100 parts by weight of the biphenol represented by formula (1) that serves as a starting material, for example, about 10 to 10,000 parts by weight, and preferably 50 to 1,000 parts by weight.

Further, it is preferred to carry out the hydrogenation reaction in the presence of a catalyst. Well-known and commonly-used hydrogenation catalysts may be used as the catalyst. Examples may include nickel catalysts such as Raney nickel, reduced nickel, and a nickel supported catalyst; cobalt catalysts such as Raney cobalt, reduced cobalt, and a cobalt supported catalyst; copper catalysts such as Raney copper; palladium catalysts such as palladium oxide, black palladium, and a carbon supported palladium catalyst; platinum catalysts such as black platinum and carbon supported platinum; rhodium catalysts, ruthenium catalysts, chromium catalysts, and copper-chromium catalysts. In the present invention, among these, from the perspectives of high catalytic activity, ease of industrial availability, and ease of separation of the catalyst from the product, it is preferred to use a nickel catalyst such as Raney nickel or a carbon supported palladium catalyst.

The amount of the catalyst to be used is, for example, based on 100 parts by weight of the biphenol represented by formula (1) that serves as a starting material, for example, about 0.1 to 50 parts by weight, and preferably 1 to 20 parts by weight.

The hydrogenation reaction is carried out at a temperature of, for example, about 20 to 180° C. (preferably 80 to 180° C., and especially preferably 100 to 180° C.), at a hydrogen pressure of, for example, about 1 to 10 MPa (preferably 3 to 8 MPa, and especially preferably 5 to 8 MPa). The reaction time is, for example, about 0.5 to 20 hours (preferably 0.5 to 10 hours, and especially preferably 0.5 to 5 hours).

After the reaction step has finished, hydrogenated biphenol can be separated and recovered from the reaction product by a common separation means such as filtration, for example. The separated and recovered hydrogenated biphenol is passed on to the purification step. The hydrogenated biphenol used in the purification step may include the solvent used in the reaction step. Alternatively, the hydrogenated biphenol can be subjected to a drying treatment to reduce the solvent content to not more than 1,000% by weight (preferably not more than 500% by weight). Further, the lower limit of the solvent content is 0% by weight. Adjusting the solvent content to the above-described range enables the recovery ratio of the hydrogenated biphenol to be improved. The purity of the hydrogenated biphenol used in the purification step is about 90 to 98.5%.

[Purification Step]

The purification step in the present invention is a step in which the reaction product obtained after the above-described reaction step is washed or crystallized using an aromatic hydrocarbon.

The above-described purification method using an aromatic hydrocarbon includes a below-described washing method and crystallization method.

Washing method: Method in which the reaction product is separated and recovered by washing with an aromatic hydrocarbon as a poor solvent.

Crystallization method: Method in which the reaction product is separated and recovered by dissolving the reaction product in a good solvent of hydrogenated biphenol (a solvent having a high degree of solubility) by heating, adding an aromatic hydrocarbon as a poor solvent thereto, and then cooling to cause the target compound to precipitate.

The washing method in the present invention is characterized by washing with an aromatic hydrocarbon, which is a poor solvent (a solvent having a low degree of solubility), without performing a step of dissolving in a good solvent of hydrogenated biphenol. For example, the washing method is carried out by suspending hydrogenated biphenol in an aromatic hydrocarbon and stirring. Since in the washing method of the present invention an aromatic hydrocarbon is used for washing from among poor solvents, an excellent washing effect can be exhibited even without performing a step for once dissolving the hydrogenated biphenol (i.e., even in a state in which the hydrogenated biphenol is still suspended in a poor solvent). The amount of the aromatic hydrocarbon to be used is, based on 1 part by weight of hydrogenated biphenol, for example, 2 to 20 parts by weight, preferably 3 to 10 parts by weight, and especially preferably 4 to 8 parts by weight.

The washing temperature is, for example, not less than −20° C. (e.g., −20° C. to 200° C.), preferably 0° C. to 140° C., more preferably 10° C. to 100° C., especially preferably 30° C. to 100° C., and most preferably 40° C. to 90° C. The purity of hydrogenated biphenol obtained by purification by washing depends on the washing temperature. By washing at a temperature within the above-described range, hydrogenated biphenol having a very high purity can be obtained. The washing time is, for example, 1 to 20 hours, preferably 2 to 15 hours, and especially preferably 3 to 10 hours.

Further, the washing may be carried out under pressure, under ordinary pressure, or under reduced pressure. In the present application, it is preferred to carry out the washing under ordinary pressure from the perspective that the washing can be carried out using general-purpose equipment, which is industrially advantageous. After washing, the hydrogenated biphenol can be separated and recovered by a well-known and commonly-used method (e.g., filtration and decantation) as necessary. The recovered hydrogenated biphenol is subsequently subjected to treatments such as drying.

Examples of the aromatic hydrocarbon used in the washing include benzene, toluene, xylene, mesitylene, and 1,3,4-trimethylbenzene (pseudocumene). In the present invention, among these, a compound in which 1 to 3 of the hydrogen atoms of a benzene have been substituted with an aliphatic hydrocarbon group (especially, an alkyl group having 1 to 3 carbon atoms) is preferred. Of such compounds, a compound in which 1 to 3 of the hydrogen atoms of a benzene such as toluene, xylene, and 1,3,4-trimethylbenzene (pseudocumene) have been substituted with a methyl group is preferred, and from the perspectives of having a high boiling point and enabling the temperature of the system to be increased, 1,3,4-trimethylbenzene (pseudocumene) is most preferred.

The crystallization method in the present invention is carried out by, utilizing the temperature dependency of the degree of solubility, adding a good solvent to the hydrogenated biphenol obtained by the hydrogenation step and heating to dissolve, then adding an aromatic hydrocarbon as a poor solvent, then cooling to cause hydrogenated biphenol having improved purity to precipitate, and separating and recovering the hydrogenated biphenol by a well-known and commonly-used method such as filtration. The recovered hydrogenated biphenol is subsequently subjected to treatments such as drying.

Examples of the good solvent of hydrogenated biphenol used in the crystallization include carboxylic acids such as acetic acid and propionic acid, and aliphatic alcohols such as methyl alcohol, ethyl alcohol, n-propyl alcohol, isopropyl alcohol (2-propanol), n-butyl alcohol, s-butyl alcohol, t-butyl alcohol, n-amyl alcohol, isoamyl alcohol, n-hexyl alcohol, n-heptyl alcohol, and n-octyl alcohol. Among these, from the perspectives of excellent solubility of the substrate and being able to use the same solvent as in the reaction step, it is especially preferred to use a lower saturated aliphatic carboxylic acid such as acetic acid, or a primary saturated aliphatic alcohol such as ethyl alcohol and 2-propanol. These solvents can be used singly or in combinations of two or more.

Examples of the aromatic hydrocarbon used in the crystallization can include the same examples as used in the above-described washing. Of these, toluene and 1,3,4-trimethylbenzene (pseudocumene) are preferred, and from the perspectives of having a high boiling point and enabling the temperature of the system to be increased, 1,3,4-trimethylbenzene (pseudocumene) is especially preferred.

The recovery ratio of the hydrogenated biphenol obtained after the purification step according to the present invention is, for example, not less than 75% (e.g., 75 to 100%), preferably not less than 90% (e.g., 90 to 100%), and especially preferably not less than 98% (e.g., 98 to 100%).

The purity of the hydrogenated biphenol obtained after the purification step according to the present invention is, for example, not less than 95% (e.g., 95 to 100%), and especially preferably not less than 99% (e.g., 99 to 100%).

According to the method for producing hydrogenated biphenol according to the present invention, since purification is carried out using an aromatic hydrocarbon, hydrogenated biphenol having a very high purity can be obtained at an excellent recovery ratio. Further, it is especially preferred to carry out the purification by washing, because very high-purity hydrogenated biphenol can be obtained at an excellent recovery ratio even without performing a special operation such as concentration or cooling.

[Method for Producing Bicyclohexene]

The method for producing bicyclohexene according to the present invention is characterized by producing hydrogenated biphenol by the above-described method for producing hydrogenated biphenol, and then dehydrating the obtained hydrogenated biphenol to obtain a corresponding bicyclohexene.

The dehydration can be carried out using a well-known and commonly used alcohol dehydration method. Examples of such a method include an alcohol dehydration method that uses an inorganic acid such as concentrated sulfuric acid or phosphoric acid as a catalyst, and an alcohol dehydration method that uses potassium bisulfate ($KHSO_4$), which is an acidic salt.

After the reaction has finished, the reaction product can be separated and purified by separation and purification means such as filtration, concentration, distillation, extraction, crystallization, recrystallization, adsorption and, column chromatography, or a combination thereof.

Examples of the bicyclohexene obtained by dehydrogenating the hydrogenated biphenol represented by formula (2) can include the compounds represented by the following formulae (3a) to (3f).

[Formula 5]

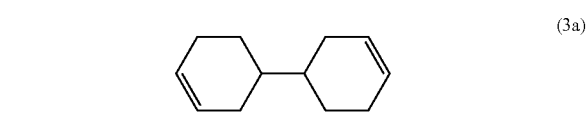

(3a)

(3b)

(3c)

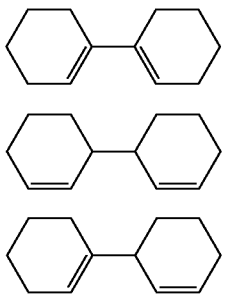

For example, bicyclohexene represented by the above formula (3a) can be obtained as a main product by dehydrogenating 4,4'-bicyclohexanol.

Further, the bicyclohexene can be preferably used as a fine chemical intermediate for pharmaceuticals, agricultural chemicals, electronic materials, and the like.

EXAMPLES

Although the present invention will now be specifically described based on the following Examples, the present invention is not limited to these Examples.

Measurement of the purity (%) of the 4,4'-biphenol, 4,4'-bicyclohexanol, and bicyclohexene was carried out using gas chromatography under an increased temperature condition of 200 to 250° C.

Production Example 1

A 300-mL autoclave equipped with a stirring device was charged with 20 g of 4,4'-biphenol, 1 g of Raney nickel, and 80 g of 2-propanol, and a hydrogenation reaction was carried out for 2 hours at a hydrogen pressure of 6 MPa and a reaction temperature of 150° C. 2-Propanol was added to the obtained reaction solution until the crystals had completely dissolved. Then, filtration was carried out to obtain a reaction product solution from which the catalyst had been removed.

Then, 21.4 g of crude 4,4'-bicyclohexanol (A) (purity: 96.7%) was obtained by concentrating and drying this reaction product solution.

Example 1

A 100-mL four-necked glass flask equipped with a stirring device and a thermometer was charged with 5.0 g of the crude 4,4'-bicyclohexanol (A) obtained in Production Example 1 and 95 g of toluene, and the resultant mixture was stirred and washed for 4 hours at 95° C. The mixture was then cooled to room temperature (25° C.), and the crystals were filtered and rinsed with toluene. The crystals were then vacuum dried to remove the toluene, whereby 4.75 g of 4,4'-bicyclohexanol (recovery ratio: 95%, purity: 99.6%) was obtained.

Comparative Example 1

A 500-mL four-necked glass flask equipped with a stirring device and a thermometer was charged with 18.7 g of the crude 4,4'-bicyclohexanol (A) obtained in Production Example 1 and 280 g of 2-propanol, and the resultant solid matter was dissolved by increasing the temperature to 80° C. Then, the mixture was concentrated by heating until the amount of 2-propanol distilled was 240 g. Heating was then stopped, and the mixture was cooled to room temperature (25° C.) to cause crystals to precipitate.

The obtained crystals were separated by filtration, rinsed with 2-propanol, and then vacuum dried to obtain 13.4 g of 4,4'-bicyclohexanol (recovery ratio: 73%, purity: 98.8%).

Comparative Example 2

A 300-mL four-necked glass flask equipped with a stirring device and a thermometer was charged with 20.7 g of the crude 4,4'-bicyclohexanol (A) obtained in Production Example 1 and 145 g of 2-propanol, and the resultant solid matter was dissolved by increasing the temperature to 80° C. Then, the mixture was cooled to room temperature (25° C.) to cause crystals to precipitate.

The obtained crystals were separated by filtration, rinsed with 2-propanol, and then vacuum dried to obtain 7.2 g of 4,4'-bicyclohexanol (recovery ration: 36%, purity: 98.9%).

Example 2

A 300-mL four-necked glass flask equipped with a stirring device and a thermometer was charged with 10.4 g of crude 4,4'-bicyclohexanol (B) (purity: 98.1%) and 190 g of toluene, and the resultant mixture was stirred and washed for 4 hours at 95° C. The mixture was then cooled to room temperature (25° C.), and the crystals were filtered and rinsed with toluene. The crystals were then vacuum dried to remove the toluene, whereby 4,4'-bicyclohexanol (recover ratio: 96%, purity: 99.8%) was obtained.

Example 3

4,4'-Bicyclohexanol (recovery ratio: 97%, purity: 99.2%) was obtained in the same manner as in Example 2, except that the washing temperature was changed from 95° C. to 25° C.

Example 4

4,4'-Bicyclohexanol (recovery ratio: 99%, purity: 99.6%) was obtained in the same manner as in Example 2, except that 40 g of 1,3,4-trimethylbenzene was used instead of 190 of toluene.

Example 5

4,4'-Bicyclohexanol (recovery ratio: 99%, purity: 99.7%) was obtained in the same manner as in Example 2, except that 40 g of 1,3,4-trimethylbenzene was used instead of 190 g of toluene and the washing temperature was changed from 95° C. to 60° C.

Example 6

A slurry was obtained by mixing 19.0 g of crude 4,4'-bicyclohexanol (C) (purity: 92.4%) and 793 g of 2-propanol, and concentrating the resultant mixture using a rotary evaporator until the total amount reached 90.7 g.

The obtained slurry was charged with 80 g of 1,3,4-trimethylbenzene, and the resultant mixture was heated to 80° C., whereby a solution was obtained. Low boiling point components were removed by distillation from the obtained solution, and distillation was continued until the system internal temperature reached 93° C. Then, the mixture was cooled to room temperature (25° C.), filtered, and dried under reduced pressure to obtain 4,4'-bicyclohexanol (recovery ratio: 92%, purity: 99.6%).

TABLE 1

| | Purification Method | Target Compound Purity (%) | Target Compound Recovery Ratio (%) |
|---|---|---|---|
| Example 1 | Washing with toluene | 99.6 | 95 |
| Example 6 | Crystallization with 1,3,4-trimethylbenzene (concentration and cooling) | 99.6 | 92 |
| Comparative Example 1 | Crystallization with good solvent (concentration and cooling) | 98.8 | 73 |
| Comparative Example 2 | Crystallization with good solvent (concentration) | 98.9 | 36 |

Example 7

A 10-liter four-necked flask equipped with a stirring device, a 20-stage distillation column, and a thermometer was charged with 6 kg of 4,4'-bicyclohexanol and 620 g of potassium bisulfate. Then, the flask was heated to 180° C. to cause the 4,4'-bicyclohexanol to melt, and stirring was started. The reaction was continued while by-product water was distilled out from the top of the distillation column. After 3 hours had elapsed, the internal pressure in the system was reduced to 10 Torr, and water and bicyclohexene were continuously distilled out of the system from the highest stage of the distillation column. The water and bicyclohexene distilled out of the system were separated into two layers with a decanter, and just the supernatant was collected. Then, the reaction temperature was increased to 220° C. over 4 hours, and the reaction was ended at the point when distillation of the water and bicyclohexene finished. The yield of crude bicyclohexene distillate was 4,507 g, and the purity as measured by gas chromatography was 98%.

4,500 g of the thus-obtained crude bicyclohexene distillate was charged into a 5-liter four-necked flask equipped with a stirring device, a 20-stage distillation column, and a thermometer and the temperature was increased to 180° C. with an oil bath. The internal pressure in the system was then reduced to 10 Torr, and after the water was distilled off, the temperature of the highest stage of the distillation column was maintained at 145° C., and the bicyclohexene was purified over 5 hours at a reflux ratio of 1 to obtain a colorless, transparent liquid. The yield of the obtained purified product of bicyclohexene was 4,353 g, and the purity as measured by gas chromatography was 99.6%.

As is clear from the Examples and Comparative Examples, for crystallization that uses 2-propanol, which is a good solvent, as the solvent, the crystal recovery ratio was not sufficient with just a cooling operation, and even when a cooling operation and a concentration operation were carried out, a satisfactory recovery ratio still was not obtained.

On the other hand, according to the method of the present invention, since an aromatic hydrocarbon, which is a poor solvent, is used, hydrogenated biphenol having a very high purity of more than 99% was obtained at an excellent recovery ratio of not less than 90% even by carrying out only a washing operation.

Further, even when using crude hydrogenated biphenol having a lower purity, hydrogenated biphenol having a very high purity of more than 99% was obtained at an excellent recovery ratio of not less than 90% by carrying out crystallization using an aromatic hydrocarbon.

Namely, according to the method of the present invention, hydrogenated biphenol having a very high purity can be obtained at an excellent recovery ratio.

INDUSTRIAL APPLICABILITY

According to the method for producing hydrogenated biphenol according to the present invention, hydrogenated biphenol having a very high purity can be efficiently produced by a simple operation. Consequently, the method for producing hydrogenated biphenol according to the present invention can be preferably used when producing high-purity hydrogenated biphenol on an industrial scale.

The invention claimed is:

1. A method for producing hydrogenated biphenol by hydrogenating biphenol represented by the following formula (1):

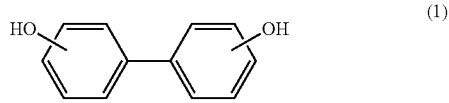

to obtain hydrogenated biphenol represented by the following formula (2):

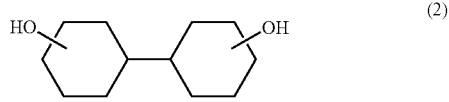

the method comprising:

a reaction step of hydrogenating the biphenol represented by formula (1); and a purification step of washing the hydrogenated biphenol of formula (2) obtained from the reaction step with a solvent comprising an aromatic hydrocarbon.

2. The method for producing hydrogenated biphenol according to claim 1, wherein the biphenol is 4,4'-biphenol and the hydrogenated biphenol is 4,4'-bicyclohexanol.

3. The method for producing hydrogenated biphenol according to claim 1 or 2, wherein the aromatic hydrocarbon is toluene or 1,3,4-trimethylbenzene.

4. A method for producing bicyclohexene, wherein hydrogenated biphenol is produced by the method according to claim 1, and the obtained hydrogenated biphenol is dehydrated to obtain a corresponding bicyclohexene.

5. A method for producing bicyclohexene, wherein hydrogenated biphenol is produced by the method according to claim 2, and the obtained hydrogenated biphenol is dehydrated to obtain a corresponding bicyclohexene.

6. A method for producing bicyclohexene, wherein hydrogenated biphenol is produced by the method according to claim 3, and the obtained hydrogenated biphenol is dehydrated to obtain a corresponding bicyclohexene.

7. A method for producing hydrogenated biphenol by hydrogenating biphenol represented by the following formula (1):

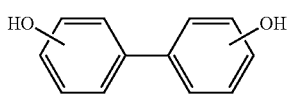 (1)

to obtain hydrogenated biphenol represented by the following formula (2):

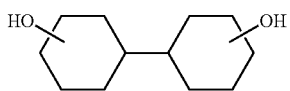 (2)

the method comprising:
a reaction step of hydrogenating the biphenol represented by formula (1); and
a purification step of crystallizing the hydrogenated biphenol of formula (2) obtained from the reaction step by dissolving in a good solvent and adding a solvent comprising aromatic hydrocarbon as a poor solvent.

8. The method for producing hydrogenated biphenol according to claim 7, wherein the biphenol is 4,4'-biphenol and the hydrogenated biphenol is 4,4'-bicyclohexanol.

9. The method for producing hydrogenated biphenol according to claim 7 or 8, wherein the aromatic hydrocarbon is toluene or 1,3,4-trimethylbenzene.

10. A method for producing bicyclohexene, wherein hydrogenated biphenol is produced by the method according to claim 7, and the obtained hydrogenated biphenol is dehydrated to obtain a corresponding bicyclohexene.

11. A method for producing bicyclohexene, wherein hydrogenated biphenol is produced by the method according to claim 8, and the obtained hydrogenated biphenol is dehydrated to obtain a corresponding bicyclohexene.

12. A method for producing bicyclohexene, wherein hydrogenated biphenol is produced by the method according to claim 9, and the obtained hydrogenated biphenol is dehydrated to obtain a corresponding bicyclohexene.

* * * * *